(12) United States Patent
Lee (10) Patent No.: US 11,577,047 B2
(45) Date of Patent: Feb. 14, 2023

(54) ESSENTIAL OIL DIFFUSION MECHANISM AND AROMATHERAPY DEVICE

(71) Applicant: PUZHEN LIFE CO., LTD., Shatin (HK)

(72) Inventor: Andy Lee, Shatin (HK)

(73) Assignee: PUZHEN LIFE CO., LTD., Shatin (HK)

(*) Notice: Subject to any disclaimer, the term of this patent is extended or adjusted under 35 U.S.C. 154(b) by 267 days.

(21) Appl. No.: 16/833,320

(22) Filed: Mar. 27, 2020

(65) Prior Publication Data
US 2021/0178111 A1 Jun. 17, 2021

(30) Foreign Application Priority Data
Dec. 17, 2019 (CN) .......................... 201922303068.8

(51) Int. Cl.
*A61M 21/02* (2006.01)
*A61M 11/02* (2006.01)
*A61M 21/00* (2006.01)

(52) U.S. Cl.
CPC ............ *A61M 21/02* (2013.01); *A61M 11/02* (2013.01); *A61M 2021/0016* (2013.01)

(58) Field of Classification Search
CPC .... A61M 11/002; A61M 11/02; A61M 11/06; A61M 11/08; A61M 15/08; A61M 2021/0016; A61M 21/02; A61M 2205/07; B05B 11/061; B05B 12/082
See application file for complete search history.

(56) References Cited

U.S. PATENT DOCUMENTS

| | | | |
|---|---|---|---|
| 9,211,357 B1* | 12/2015 | Li | A61M 11/06 |
| 9,421,295 B1* | 8/2016 | Li | A61L 9/12 |
| 2002/0068023 A1* | 6/2002 | Davis | A61L 9/14 |
| | | | 422/124 |
| 2012/0018530 A1* | 1/2012 | Blaylock | A61L 9/14 |
| | | | 239/338 |

* cited by examiner

*Primary Examiner* — Christine H Matthews
(74) *Attorney, Agent, or Firm* — Robert L. Stearns; Dickinson Wright, PLLC (57) ABSTRACT

An essential oil diffusion mechanism, including: a housing having an accommodation chamber; and a separator that divides the accommodation chamber into an upper chamber and a lower chamber and includes a horizontal partition plate and vertical partition plates. The horizontal partition plate defines at least one interconnecting hole. An upper surface of each vertical partition plate is spaced apart from a chamber wall of the upper chamber to form an upper interconnecting aperture. Each vertical partition plate defines an interconnecting reflux hole. A lower surface of each baffling plate is spaced apart from the horizontal partition plate to form a lower interconnecting aperture. The interconnecting hole, the upper interconnecting aperture, the lower interconnecting aperture, and the air outlet are sequentially arranged in communication to form an air outlet channel. The upper interconnecting aperture, the reflux hole, and the interconnecting hole are sequentially arranged in communication to form a reflux channel.

18 Claims, 7 Drawing Sheets

ESSENTIAL OIL DIFFUSION MECHANISM AND AROMATHERAPY DEVICE

CROSS-REFERENCE TO RELATED APPLICATION

The present application claims priority to Chinese Patent Application Ser. No. CN201922303068.8, filed on Dec. 17, 2019, the entire content of which is incorporated herein by reference in its entirety.

BACKGROUND

Technical Field

The present disclosure relates to the technical field of daily necessities, and particularly relates to an essential oil diffusion mechanism and an aromatherapy device.

Description of Related Art

A typical aromatherapy device includes an oil storage vial for storing essential oil, and an atomizer for atomizing the essential oil. Some aromatherapy devices may also be equipped with air pumps to mix the essential oil with air to further diffuse the essential oil during the atomization of the essential oil. The atomizer atomizes the essential oil, so that the essential oil is broken up into small particles and can float with the air. However, inevitably, in this process some larger particles still exist. These larger particles are directly discharged into the air. Due to the heavy weight, they are attached to the periphery of the air outlet and it is difficult to diffuse to a large extent, causing a waste of essential oil.

SUMMARY

In view of the above-described problems, it is an object of the present application to provide an essential oil diffusion mechanism and aromatherapy device, which aims to reduce the waste of essential oil.

To achieve the above object, the present disclosure is realized as follows:

An essential oil diffusion mechanism, is configured to match with an essential oil gasification mechanism, the essential oil gasification mechanism is provided with an oil outlet configured for outputting an essential oil. The essential oil diffusion mechanism comprises:

a housing, the housing comprising: an accommodation chamber and an air outlet in communication with the accommodation chamber and the outside; and the housing being provided with baffling plates by the side of the air outlet;

a separator, arranged in the accommodation chamber and dividing the accommodation chamber into an upper chamber and a lower chamber; the separator comprising: a horizontal partition plate, and vertical partition plates arranged on an upper surface of the horizontal partition plate; the horizontal partition plate defining therein at least one interconnecting hole configured for communicating with the upper chamber and the lower chamber; an upper surface of each vertical partition plate being spaced apart from a chamber wall of the upper chamber to form an upper interconnecting aperture; and each vertical partition plate defining an interconnecting reflux hole in a lower end portion thereof.

The lower chamber is configured to communicate with the oil outlet; a lower surface of each baffling plate is spaced apart from the horizontal partition plate to form a lower interconnecting aperture. The interconnecting hole, the upper interconnecting aperture, the lower interconnecting aperture, and the air outlet are sequentially arranged in communication to form an air outlet channel. The upper interconnecting aperture, the reflux hole, and the interconnecting hole are sequentially arranged in communication to form a reflux channel.

In an embodiment, the air outlet is arranged in the center, at least two interconnecting holes are provided and located outside the air outlet, and the horizontal partition plate is arranged obliquely towards a direction of each interconnecting hole.

In an embodiment, two interconnecting holes are provided and symmetrically arranged in the left and the right. A plane formed between a front/rear plate edge and the center of the horizontal partition plate is inclined inwards, and a plane formed between a left/right plate edge and the center of the horizontal partition plate is inclined outward.

In an embodiment, each vertical partition plate is a straight plate and extends in a front-rear direction.

In an embodiment, the baffling plate is a straight plate and is arranged in parallel with the vertical partition plate.

In an embodiment, the reflux hole extends downward to an upper surface of the horizontal partition plate.

In an embodiment, the separator further comprises at least one guide post connected to a lower surface of the horizontal partition plate; and the at least one guide post is arranged along a periphery of the interconnecting hole.

In an embodiment, the housing comprises: a housing seat, a liner, and an upper cover; the upper cover and the housing seat are snap fitted and enclosed with each other to form an accommodation chamber; the housing seat has a ring-shaped platform, which is parallel to an upper surface of the housing seat, and the liner and the separator are nested up and down and placed on the platform together; the upper cover and the housing seat are snap fitted with each other to fix the liner and the separator in the accommodation chamber; the liner defines a first through hole in the middle, and the upper cover defines a second through hole at a position corresponding to the first through hole, such that the first through hole and the second through hole form the air outlet; the liner and the separator are nested up and down to form an upper chamber, and a baffling plate is arranged above the separator.

In an embodiment, an upper surface of the liner is recessed downward to form blind holes, and the upper cover is provided with inserts at positions corresponding to those of the blind holes. The number of the blind holes is two; convex pillars are formed on a lower surface of the liner at positions corresponding to those of the blind holes, and the convex pillars are located by a front side and a rear side of the air outlet.

An aromatherapy device, comprising the essential oil diffusion mechanism as described above.

The essential oil diffusion mechanism provided by the present disclosure increases the path and difficulty of the diffusion of essential oil to the air outlet through the reasonable arrangement of the air outlet channel, thereby reducing the waste of essential oil and increasing the amount of essential oil recovery of larger particles.

BRIEF DESCRIPTION OF THE DRAWINGS

In order to explain the technical schemes in the embodiments of the present disclosure more clearly, the drawings used in the embodiments will be briefly introduced below. Obviously, the drawings in the following description are only some embodiments of the present disclosure. For those of ordinary skill in the art, other drawings can be obtained based on these drawings without devoting creative labor.

DESCRIPTION OF REFERENCE NUMERALS OF THE DRAWINGS

| Reference numerals | Designation | Reference numerals | Designation |
| --- | --- | --- | --- |
| 10 | Housing | 20 | Separator |
| 11 | Housing seat | 21 | Horizontal partition plate |
| 12 | Liner | 22 | Vertical partition plate |
| 121 | Convex pillar | 211 | Interconnecting hole |
| 13 | Upper cover | 221 | Upper interconnecting aperture |
| 131 | Flange | 222 | Reflux hole |
| 132 | Insert | 23 | Guide post |
| 14 | Air outlet | 30 | Essential oil gasification mechanism |
| 15 | Baffling plate | 31 | Oil storage vial |
| 151 | Lower interconnecting aperture | 32 | Atomizer |
| 16 | Seal ring | 33 | Air pump |
| 101 | Upper chamber | | |
| 102 | Lower chamber | | |

DETAILED DESCRIPTION OF THE EMBODIMENTS

In order to make the purpose, technical scheme, and advantages of the present disclosure clearer, the present disclosure is further described in detail below with reference to the accompanying drawings and embodiments. It should be understood that the specific embodiments described herein are only used to explain the present disclosure and are not intended to limit the present disclosure.

It should be noted that when one component is called to be "fixed to" or "arranged on" another component, it may be directly on the other component or indirectly on the other component. When one component is referred to as being "connected to" another component, it can be directly connected to the other component or indirectly connected to the other component.

In addition, the terms "first" and "second" are used for descriptive purposes only and cannot be understood as indicating or implying relative importance or implicitly indicating the number of technical features indicated. Therefore, the features defined as "first" and "second" may explicitly or implicitly include one or more of the features.

In the description of the present disclosure, the meaning of "a plurality of" is two or more, unless it is specifically defined otherwise.

Figure 1:
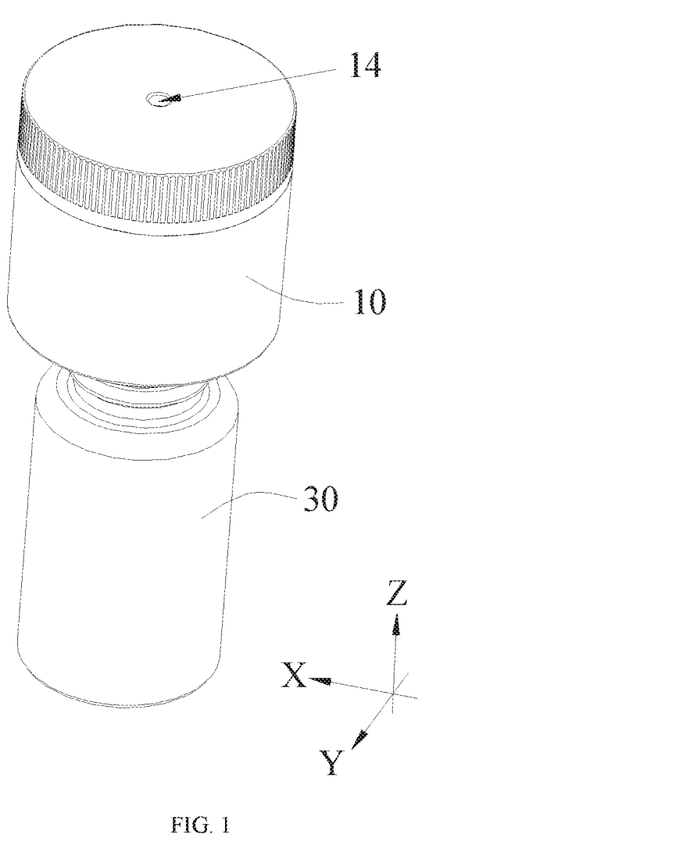
FIG. 1 is a perspective view of an essential oil diffusion mechanism and an essential oil gasification mechanism according to an embodiment of the present disclosure.

It should also be noted that, in the embodiment of the present disclosure, according to the XYZ rectangular coordinate system established in FIG. 1, the side located in the positive direction of the X axis is defined as the front side, and the side located in the negative direction of the X axis is defined as the rear side; the side located in the positive direction of the Y axis is defined as the left side, the side located in the negative direction of the Y axis is defined as the right side, the side located in the positive direction of the Z axis is defined as the upper side, and the side located in the negative direction of the Z axis is defined as the lower side.

It should also be noted that the terms of "left", "right," "upper", and "lower" in the embodiments of the present disclosure are merely relative concepts or reference to the normal use status of the product, and should not be considered as limiting thereof.

Example 1

Referring to FIGS. 1-7, the present example provides an essential oil diffusion mechanism, which is configured for matching with an essential oil gasification mechanism 30.

The essential oil gasification mechanism 30 includes: an oil storage vial 31, an atomizer 32, and an air pump 33. The oil storage vial 31 is used to store an essential oil. The atomizer 32 is connected to the oil storage vial 31. The atomizer 32 has an oil outlet. The atomizer 32 atomizes the essential oil from the oil vial 31 and sprays the essential oil out through the oil outlet. The air pump 33 is arranged outside the oil outlet and is used to output air towards the oil outlet to mix air into the essential oil, thereby promoting the diffusion of the essential oil. Only a partial structure of the air pump 33 is shown in the figure.

The essential oil diffusion mechanism is used to diffuse a vaporized essential oil generated by the essential oil gasification mechanism 30 into the air. The vaporized essential oil diffusion mechanism includes: a housing 10 and a separator 20. The housing 10 has an accommodation chamber and an air outlet 14 communicating with the accommodation chamber and the outside. The separator 20 is placed in the accommodation chamber, and the accommodation chamber is divided by the separator 20 into an upper chamber 101 and a lower chamber 102.

The housing 10 is provided with baffling plates 15 by the side of the air outlet 14, and a lower surface of each baffling plate 15 is spaced apart from a horizontal partition plate 21 to form a lower interconnecting aperture 151.

The separator 20 includes the horizontal partition plate 21 and vertical partition plates 22 arranged on an upper surface of the horizontal partition plate 21. The horizontal partition plate 21 defines therein at least one interconnecting hole 211 configured for communicating with the upper chamber 101 and the lower chamber 102. An upper surface of each vertical partition plate 22 is spaced apart from a chamber wall of the upper chamber 101 to form an upper interconnecting aperture 221, an interconnecting reflux hole 222 is defined in a lower end portion of each vertical partition plate 22.

The interconnecting hole 211, the upper interconnecting aperture 221, the lower interconnecting aperture 151, and the air outlet 14 are sequentially arranged in communication to form an air outlet channel; and the upper interconnecting aperture 221, the reflux hole 222, and the interconnecting hole 211 are sequentially arranged in communication to form a reflux channel.

The lower chamber 102 is configured to communicate with the oil outlet. The essential oil gasification mechanism 30 is connected to the housing 10, and the oil outlet is placed in the lower chamber 102. The essential oil gasification mechanism 30 outputs the essential oil towards the lower chamber 102. The essential oil is evacuated to the outside through the air outlet channel or returned to the lower chamber 102 through the reflux channel.

The essential oil is atomized by the atomizer 32 to form fine particles that are mixed with the air and diffuse upward, enter the upper chamber 101 through the interconnecting hole 211. As restricted by the upper chamber 101 wall of the upper chamber 101, the mixture of the fine particles and the air passes through the upper interconnecting aperture 221 and enters a space between the vertical partition plate 22 and the baffling plate 15. Thereafter, as being restricted by the baffling plate 15, the mixture of the fine particles and the air moves downward, and then passes through the lower interconnecting aperture 151 and the air outlet 14 to leave the upper chamber 101. In this process, the larger particles of the essential oil fall downwards, due to their own weights, and fall directly to the lower chamber 102 or onto the horizontal partition plate 21 and return to the lower chamber 102 through the reflux hole 222. The arrangement of the vertical partitions 22 and the baffling plate 15 effectively slows down the diffusion speed of the essential oil to the air outlet 14, thereby increasing the number of essential oil large particles falling back. In addition, due to the positions of the upper interconnecting aperture 221 and the lower interconnecting aperture 151, the air outlet channel has a process of lifting, sinking, and re-lifting, which increases the difficulty of diffusion of essential oil to air outlet 14, especially the larger particles of essential oil, which obviously increases the amount of the refluxed essential oil.

In an embodiment, the lower chamber 102 communicates with the oil storage chamber of the oil storage vial 31, and the refluxed large particles of the essential oil will flow into the oil storage chamber for recycling.

The essential oil diffusion mechanism provided in an embodiment increases the path and difficulty in the diffusion of essential oil towards the air outlet 14 through the reasonable arrangement of the air outlet channel, thereby reducing the waste of the essential oil and increasing the recovery amount of the essential oil with larger particles.

In an embodiment, the movement of the essential oil to the air outlet 14 (air outlet channel) needs to pass through two blockings (the vertical partition 22 and the baffling plate 15). Those skilled in the art can also set the number of blocking or optimize the path according to their needs, such as increasing the number of vertical partitions 22 or baffling plates 15, such as adjusting the distance between upper interconnecting aperture 221 and lower interconnecting aperture 151, which is not limited here.

In an embodiment, the air outlet 14 is arranged in the center. In other embodiments, the air outlet 14 may also be arranged on the side or near the middle, as long as the air outlet channel and the reflux channel described above are formed between the air outlet 14 and the interconnecting hole 211.

The interconnecting hole 211 may be one or more than two. When there is only one interconnecting hole 211, a distance between the interconnecting hole 211 and the air outlet 14 is appropriately increased to increase a path length of the air outlet channel.

In an embodiment, the air outlet 14 is arranged in the center, at least two interconnecting holes 211 are provided and located outside the air outlet 14, and the horizontal partition plate 21 is arranged obliquely towards a direction of each interconnecting hole 211. Preferably, the interconnecting holes 211 are arranged along a plate edge of the horizontal partition plate 21 in intervals. In an embodiment, the horizontal partition plate 21 is inclined downward from the middle to the periphery, and the interconnecting holes 211 are evenly distributed on the plate edge of the horizontal partition plate 21, so that the essential oil dropping onto the horizontal partition plate 21 can directly slide toward the interconnecting holes 211 along an upper surface of the horizontal partition plate 21.

Figure 3:
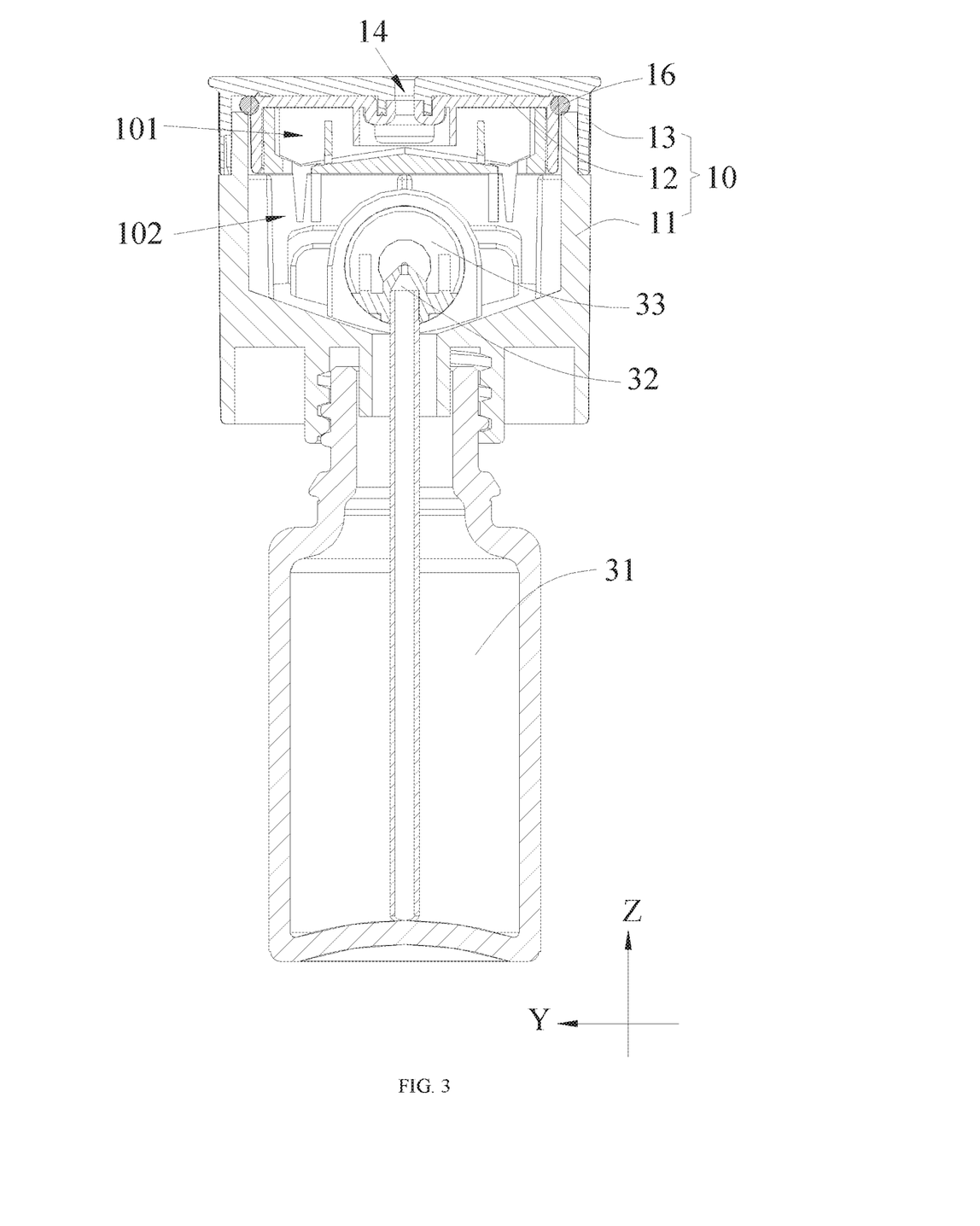
FIG. 3 is a cross-sectional view of the essential oil diffusion mechanism and the essential oil gasification mechanism at an air outlet and along a YZ plane.
Figure 4:
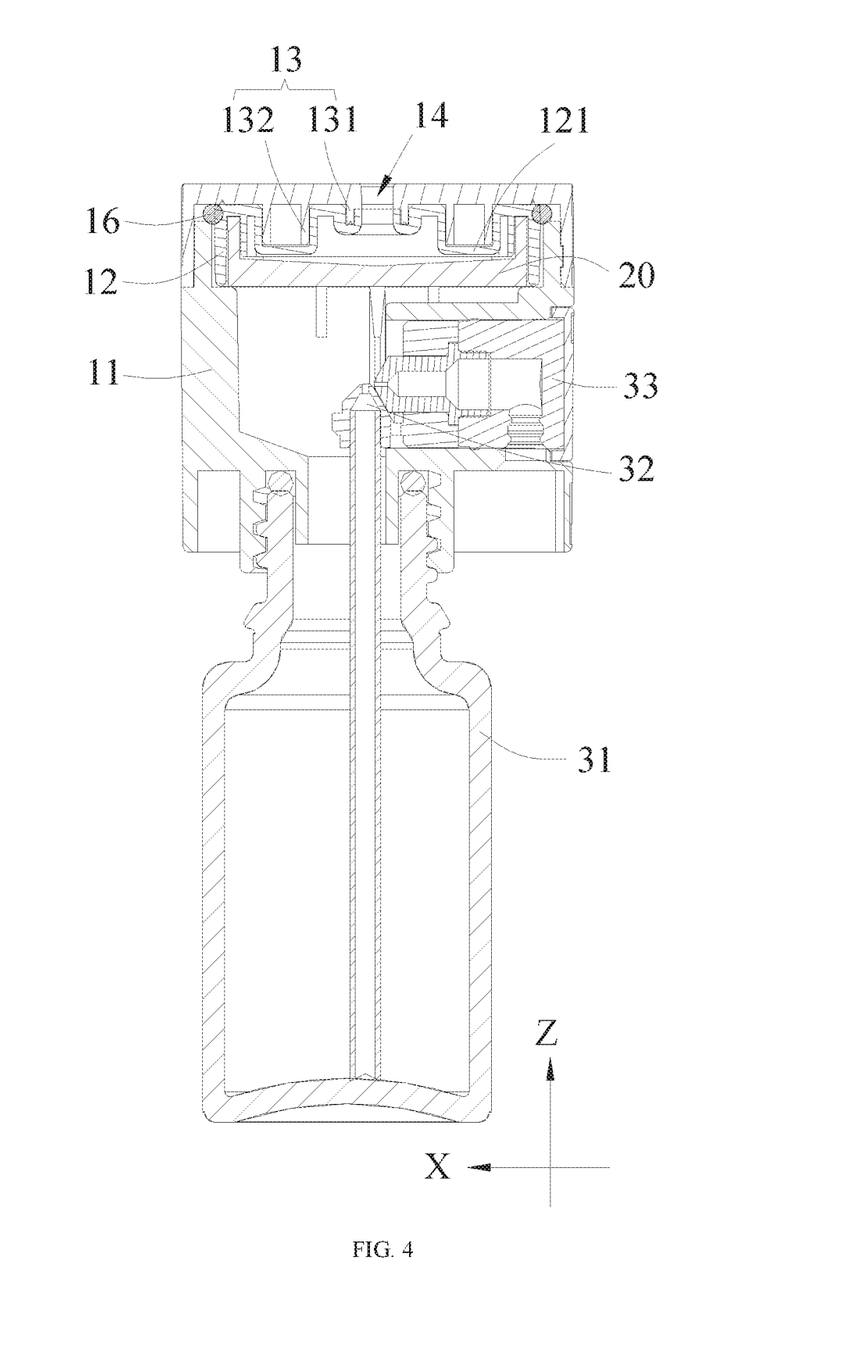
FIG. 4 is a cross-sectional view of the essential oil diffusion mechanism and the essential oil gasification mechanism at the air outlet and along an XZ plane.
Figure 5:
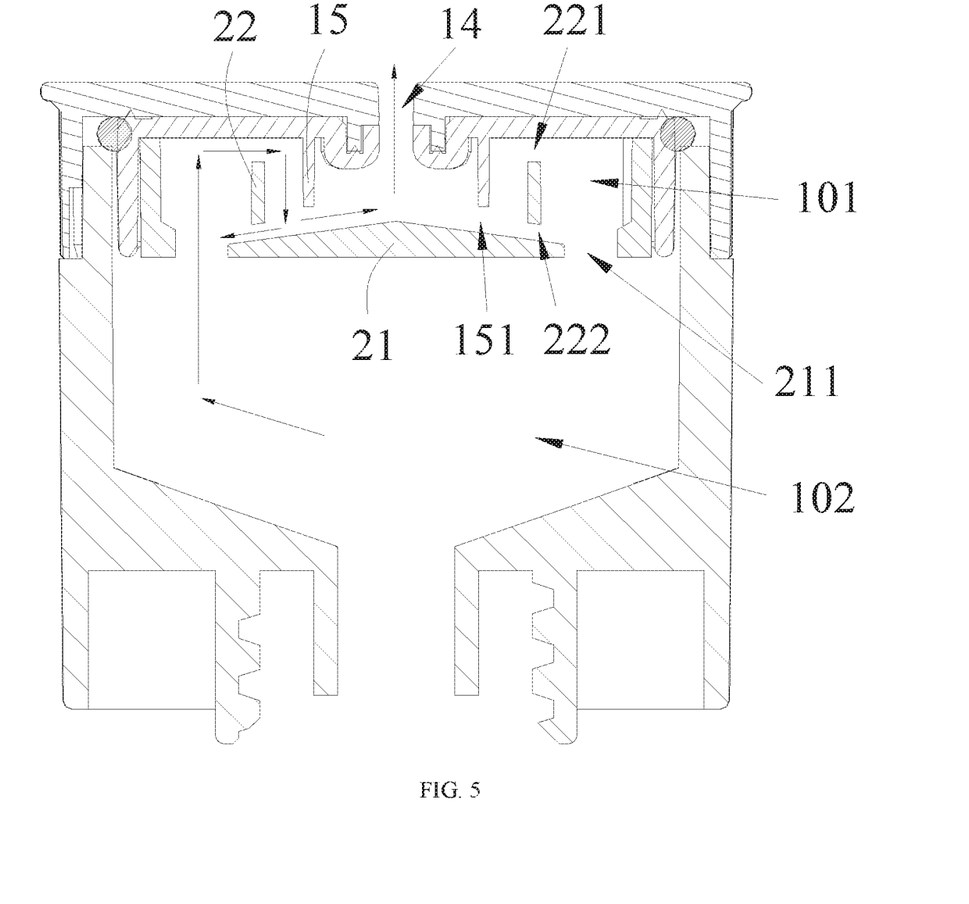
FIG. 5 is a cross-sectional view of the essential oil diffusion mechanism at the air outlet and along the YZ plane.

In an embodiment, two interconnecting holes 211 are provided and are symmetrically arranged in the left and the right. Referring to FIGS. 3 and 4, a plane formed between a front/rear plate edge and the center of the horizontal partition plate 21 is inclined inwards, and a plane formed between a left/right plate edge and the center of the horizontal partition plate 21 is inclined outward. Referring to FIG. 4, the horizontal partition plate 21 is inclined to the middle in the front-rear direction. Referring to FIG. 3, the horizontal partition plate 21 is inclined to the two sides in the left-right direction, and two interconnecting holes 211 are located at the left and right ends of the horizontal partition plate 21. The essential oil dropping on the upper surface of the horizon partition plate 21, as guided by the horizon partition plate 21, moves along a central axis of either the front plate or the rear plate, and then move from the central axis towards two sides of either the front plate or the rear plate, and fall into the corresponding interconnecting hole 211. This design facilitates the collection of essential oils. In other embodiments, the two interconnecting holes 211 may also be arranged asymmetrically, which is not limited here.

Figure 7:
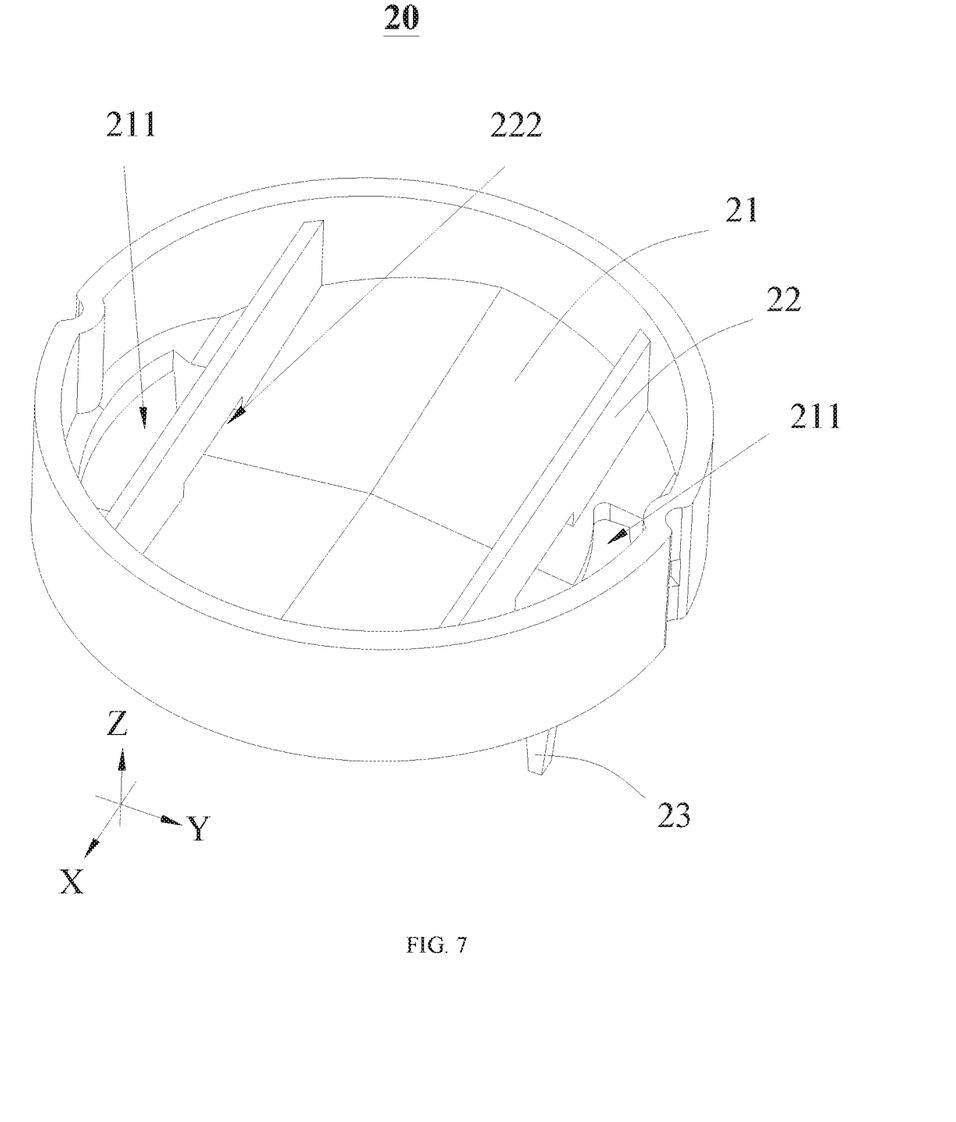
FIG. 7 is a perspective view of the separator.

Referring to FIG. 7, in an embodiment, each vertical partition plate 22 is a straight plate and extends in a front-rear direction. This design helps to simplify the structural design and reduce the processing costs. In the illustrated structure, two vertical partition plates 22 are provided and arranged at the left side and the right side of the air outlet 14. Those skilled in the art may also set the vertical partitions 22 as arc-shaped plates around the air outlet 14.

Figure 6:
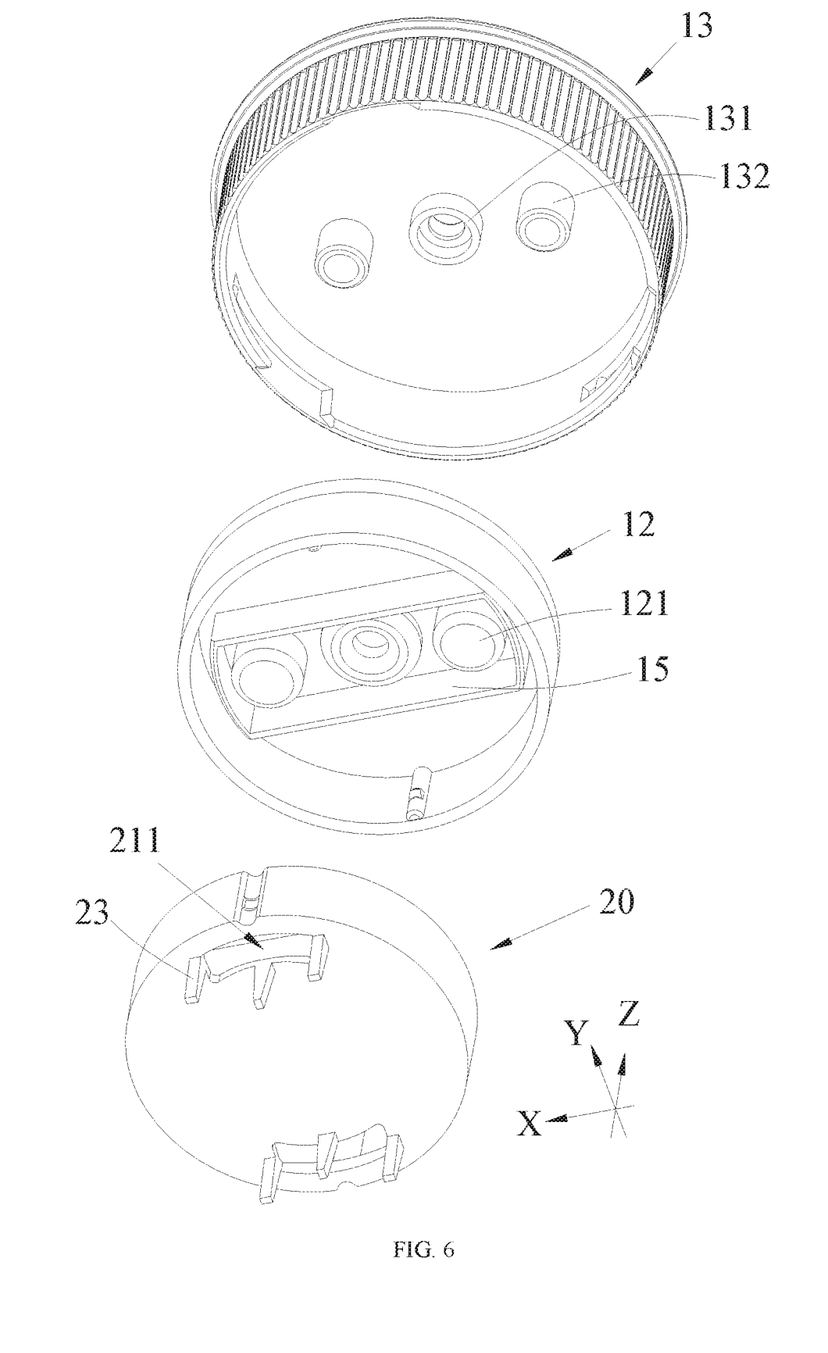
FIG. 6 is an exploded view of coordination of upper cover, liner and separator.

Referring to FIG. 6, in an embodiment, the baffling plate 15 is a straight plate and is arranged in parallel with the vertical partition plate 22. This design helps to simplify the structural design and processing costs. In the illustrated embodiment, the two baffling plates 15 are arranged on the left and right sides of air outlets 14. Those skilled in the art may also set the baffling plate 15 as arc-shaped plate around the air outlet 14.

Referring to FIG. 7, in an embodiment, the reflux hole 222 extends downward to an upper surface of the horizontal partition plate 21. This arrangement avoids a distance between a lower edge of a hole wall and the horizontal partition plate 21, which would otherwise form a step preventing the essential oil from flowing downwards along horizontal partition plate 21.

Referring to FIG. 6, in an embodiment, the separator 20 further includes at least one guide post 23 connected to a lower surface of the horizontal partition plate 21. The at least one guide post 23 is arranged along a periphery of the interconnecting hole 211. In the embodiment shown in the figure, three guide posts 23 are arranged on a periphery of each interconnecting hole, and each guide post is arranged in a prism shape and a cross section thereof is gradually tapered from top to bottom to facilitate the collection of essential oil. Those skilled in the art may also set the number, position, and shape of the guide posts 23 according to actual needs, which is not limited here.

Figure 2:
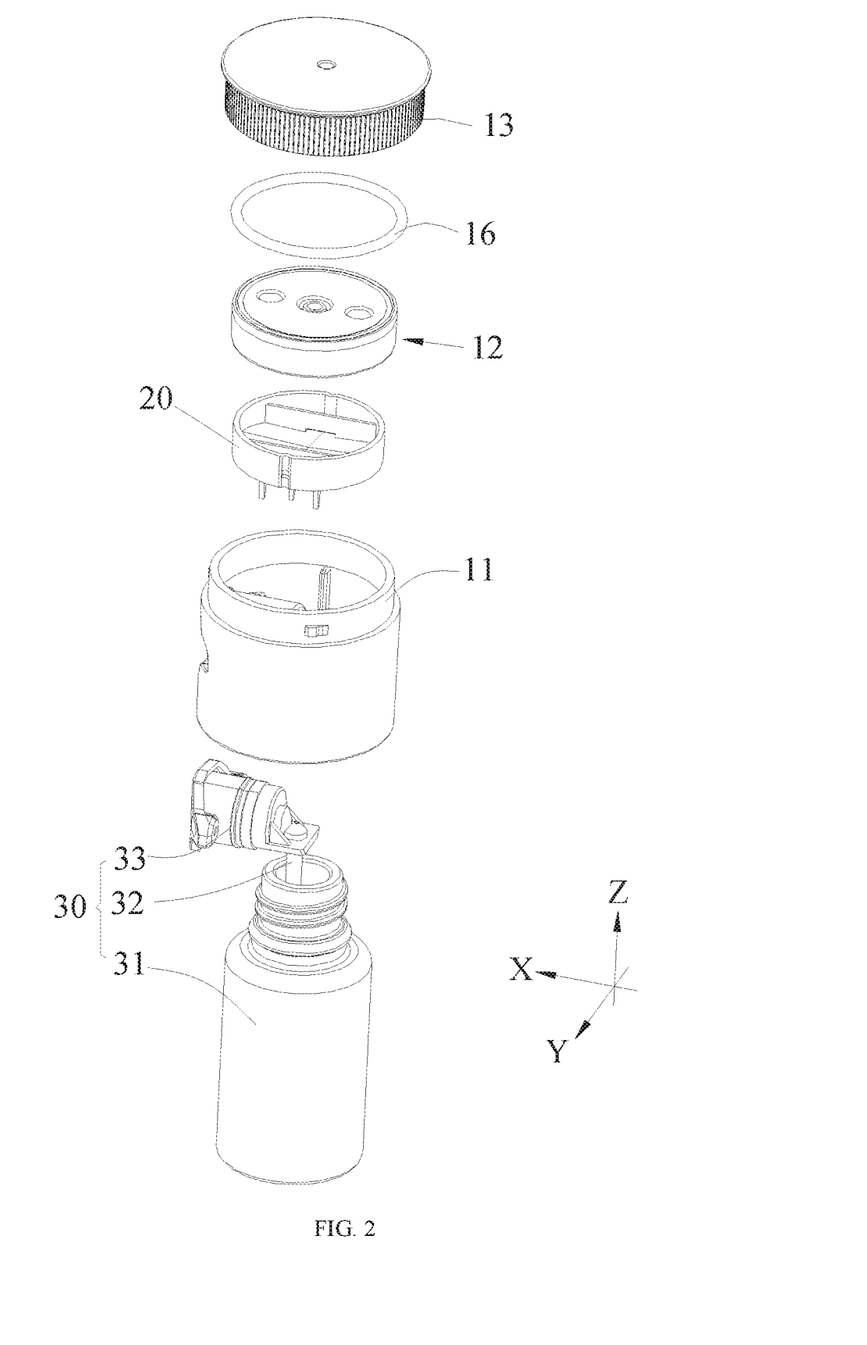
FIG. 2 is an exploded view of the essential oil diffusion mechanism and the essential oil gasification mechanism including an air pump wherein the air pump is only partially shown.

Referring to FIG. 2, the housing 10 includes: a housing seat 11, a liner 12, and an upper cover 13. The upper cover 13 and the housing seat 11 are snap fitted and enclosed with each other to form an accommodation chamber. The housing seat 11 has a ring-shaped platform, which is parallel to an upper surface of the housing seat 11, and the liner 12 and the separator 20 are nested up and down and placed on the platform together. The upper cover 13 and the housing seat 11 are snap fitted with each other to fix the liner 12 and the separator 20 in the accommodation chamber. The liner 12 defines a first through hole in the middle, and the upper cover 13 defines a second through hole at a position corresponding to the first through hole, such that the first through hole and the second through hole form the air outlet 14. The liner 12 and the separator 20 are nested up and down to form the upper chamber 101, and a baffling plate 15 is arranged above the separator 20.

In an embodiment, the housing 10 adopts multiple parts to reduce the difficulty of design and processing. The housing 10 is divided into the housing seat 11, the liner 12, and the upper cover 13. The liner 12 and separator 20 are nested together. Both the upper cover 13 and the liner 12 are also provided with structures for the nesting connection, respectively. Finally, the upper cover 13 and the housing seat 11 are snap fitted. This arrangement is helpful to improve the structure tightness of the connection.

The arrangement of the platform is used to support the separator 20 and the liner 12 and restrict the downward movement of separator 20 and liner 12.

In the illustrated embodiment, a seal ring 16 is further arranged between the upper cover 13 and the housing seat 11, and the seal ring 16 is ring-shaped, and is clamped in an accommodation space enclosed by the upper cover 13, the housing seat 11, and the liner 12, so as to improve the water-tightness of the connection.

Referring to FIGS. 3 and 4, the upper cover and the liner 12 are nested with each other. Specifically, the liner 12 is provided with a downward groove on the peripheral side of the first through hole, and the upper cover 13 is provided with a flange 131 at a position corresponding to the groove for matching the groove. The upper surface of the liner 12 is provided with an upward protrusion, and the upper cover 13 is correspondingly provided with a matching groove at a position corresponding to the protrusion. The protrusion is inserted into the matching groove, and the flange 131 is inserted into the groove, which is beneficial to improve the connection tightness between the upper cover 13 and the liner 12 while positioning. In the illustrated embodiment, both the protrusion and the flange 131 are ring-shaped structures. Those skilled in the art can setup the specific structure, shape, and position of the nested structure according to actual needs, which is not limited here.

Referring to FIG. 4, an upper surface of the liner 12 is recessed downward to form blind holes, and the upper cover 13 is provided with inserts 132 at positions corresponding to those of the blind holes. The insert 132 is inserted into the blind hole, and it is beneficial to improve the connection tightness and overall structural strength between upper cover 13 and liner 12 while positioning. In the illustrated embodiment, the number of the blind holes is two.

Referring to FIG. 6, convex pillars 121 are formed on a lower surface of the liner 12 at positions corresponding to those of the blind holes, and the convex pillars 121 are located by a front side and a rear side of the air outlet 14. The convex pillars 121 are located between two baffling plates 15. The arrangement of convex pillars 121 increases the difficulty of diffusion of essential oil and also helps increase the amount of the refluxed essential oil of larger particles.

Example 2

The present disclosure also provides an aromatherapy device. The aromatherapy device includes the essential oil diffusion mechanism of Example 1. For a specific structure of the essential oil diffusion mechanism, refer to the Example 1. Since this aromatherapy device adopts all the technical schemes of Example 1, it also has all the beneficial effects brought by the technical schemes of the above Example 1, which will not be repeated here.

The above are only the preferred embodiments of the present disclosure, and are not intended to limit the present disclosure. Any modification, equivalent replacement or improvement made within the spirit and principle of the present disclosure shall be within the protection scope of the present disclosure.

What is claimed is:

1. An essential oil diffusion mechanism, configured to be cooperatively used with an essential oil gasification mechanism, the essential oil gasification mechanism being provided with an oil outlet configured for outputting an essential oil; the essential oil diffusion mechanism comprising:
   a housing, the housing comprising: an accommodation chamber and an air outlet in communication with the accommodation chamber and an ambient environment outside the housing; and the housing being provided with baffling plates by a side of the air outlet;
   a separator, arranged in the accommodation chamber and dividing the accommodation chamber into an upper chamber and a lower chamber; the separator comprising: a horizontal partition plate, and vertical partition plates arranged on an upper surface of the horizontal partition plate; the horizontal partition plate defining therein at least one interconnecting hole configured for communicating with the upper chamber and the lower chamber; an upper surface of each vertical partition plate being spaced apart from a chamber wall of the upper chamber to form an upper interconnecting aperture; and each vertical partition plate defining an interconnecting reflux hole in a lower end portion thereof;
wherein
   the lower chamber is configured to communicate with the oil outlet; a lower surface of each baffling plate is spaced apart from the horizontal partition plate to form a lower interconnecting aperture;
   the at least one interconnecting hole, the upper interconnecting aperture, the lower interconnecting aperture, and the air outlet are sequentially arranged in communication to form an air outlet channel; and
   the upper interconnecting aperture, the reflux hole, and the at least one interconnecting hole are sequentially arranged in communication to form a reflux channel.

2. The essential oil diffusion mechanism according to claim 1, wherein the air outlet is arranged in a center of the housing, at least two interconnecting holes are provided and located outside the air outlet, and the horizontal partition plate is arranged obliquely towards a direction of each interconnecting hole.

3. The essential oil diffusion mechanism according to claim 2, wherein two interconnecting holes are provided and symmetrically arranged in a left end and a right end of the horizontal partition plate; and the horizontal partition plate is inclined to a center of the horizontal partition plate in a front-rear direction, and inclined to two sides of the horizontal partition plate in a left-right direction.

4. The essential oil diffusion mechanism according to claim 3, wherein each vertical partition plate is a straight plate and extends in the front-rear direction.

5. The essential oil diffusion mechanism according to claim 4, wherein the baffling plates are straight plates and are arranged in parallel with the vertical partitions plates.

6. The essential oil diffusion mechanism according to claim 1, wherein the reflux hole extends downward to the upper surface of the horizontal partition plate.

7. The essential oil diffusion mechanism according to claim 1, wherein the separator further comprises at least one guide post connected to a lower surface of the horizontal partition plate; and the at least one guide post is arranged along a periphery of the at least one interconnecting hole.

8. The essential oil diffusion mechanism according to claim 1, wherein the housing comprises: a housing seat, a liner, and an upper cover; the upper cover and the housing seat are snap fitted and enclosed with each other to form the accommodation chamber; the housing seat has a ring-shaped platform, which is parallel to an upper surface of the housing seat, and the liner and the separator are nested in a vertical direction and placed on the platform together; the upper cover and the housing seat are snap fitted with each other to fix the liner and the separator in the accommodation chamber; the liner defines a first through hole in a middle of the liner, and the upper cover defines a second through hole at a position corresponding to the first through hole, such that the first through hole and the second through hole form the air outlet; the liner and the separator are nested in the vertical direction to form the upper chamber; and the baffling plates are arranged above the separator.

9. The essential oil diffusion mechanism according to claim 8, wherein
an upper surface of the liner is recessed downward to form blind holes, and the upper cover is provided with inserts at positions of the upper cover corresponding to positions of the blind holes; and
the number of the blind holes is two; convex pillars are formed on a lower surface of the liner at positions of the liner corresponding to the positions of the blind holes, and the convex pillars are located by a front side and a rear side of the air outlet.

10. An aromatherapy device, comprising the essential oil diffusion mechanism according to claim 1.

11. The aromatherapy device according to claim 10, wherein the air outlet is arranged in a center of the housing, at least two interconnecting holes are provided and located outside the air outlet, and the horizontal partition plate is arranged obliquely towards a direction of each interconnecting hole.

12. The aromatherapy device according to claim 11, wherein
two interconnecting holes are provided and symmetrically arranged in a left end and a right end of the horizontal partition plate; and
the horizontal partition plate is inclined to a center of the horizontal partition plate in a front-rear direction, and inclined to two sides of the horizontal partition plate in a left-right direction.

13. The aromatherapy device according to claim 12, wherein each vertical partition plate is a straight plate and extends in the front-rear direction.

14. The aromatherapy device according to claim 13, wherein the baffling plates are straight plates and are arranged in parallel with the vertical partition plates.

15. The aromatherapy device according to claim 10, wherein the reflux hole extends downward to the upper surface of the horizontal partition plate.

16. The aromatherapy device according to claim 10, wherein the separator further comprises at least one guide post connected to a lower surface of the horizontal partition plate; and the at least one guide post is arranged along a periphery of the at least one interconnecting hole.

17. The aromatherapy device according to claim 10, wherein the housing comprises: a housing seat, a liner, and an upper cover; the upper cover and the housing seat are snap fitted and enclosed with each other to form the accommodation chamber; the housing seat has a ring-shaped platform, which is parallel to an upper surface of the housing seat, and the liner and the separator are nested in a vertical direction and placed on the platform together; the upper cover and the housing seat are snap fitted with each other to fix the liner and the separator in the accommodation chamber; the liner defines a first through hole in a middle of the liner, and the upper cover defines a second through hole at a position corresponding to the first through hole, such that the first through hole and the second through hole form the air outlet; the liner and the separator are nested in the vertical direction to form the upper chamber, and the baffling plates are arranged above the separator.

18. The aromatherapy device according to claim 17, wherein
an upper surface of the liner is recessed downward to form blind holes, and the upper cover is provided with inserts at positions of the upper cover corresponding to positions of the blind holes; and
the number of the blind holes is two; convex pillars are formed on a lower surface of the liner at positions of the liner corresponding to the positions of the blind holes, and the convex pillars are located by a front side and a rear side of the air outlet.

* * * * *